(12) United States Patent
Nielsen et al.

(10) Patent No.: US 8,638,108 B2
(45) Date of Patent: Jan. 28, 2014

(54) DEVICE AND METHOD FOR CONTACT FREE ABSOLUTE POSITION DETERMINATION

(75) Inventors: Preben Nielsen, Holbaek (DK); Bodo von Munchow, Lyngby (DK)

(73) Assignee: Novo Nordisk A/S, Bagsvaerd (DK)

( * ) Notice: Subject to any disclaimer, the term of this patent is extended or adjusted under 35 U.S.C. 154(b) by 1009 days.

(21) Appl. No.: 12/067,472

(22) PCT Filed: Sep. 22, 2006

(86) PCT No.: PCT/EP2006/009240
§ 371 (c)(1),
(2), (4) Date: Oct. 28, 2008

(87) PCT Pub. No.: WO2007/039148
PCT Pub. Date: Apr. 12, 2007

(65) Prior Publication Data
US 2009/0076460 A1    Mar. 19, 2009

Related U.S. Application Data

(60) Provisional application No. 60/720,593, filed on Sep. 26, 2005.

(30) Foreign Application Priority Data

Sep. 22, 2005    (EP) .................................... 05020657

(51) Int. Cl.
*G01R 27/26*    (2006.01)
(52) U.S. Cl.
USPC ........................................................ 324/662
(58) Field of Classification Search
USPC ................................................. 324/654–690
See application file for complete search history.

(56) References Cited

U.S. PATENT DOCUMENTS 3,700,862 A    10/1972    Snook et al.
3,809,863 A    5/1974    Oberg
(Continued)

FOREIGN PATENT DOCUMENTS

| CN | 1013704 | 8/1991 |
|---|---|---|
| CN | 1051152 | 9/1993 |
| DE | 1950411 | 11/1966 |
| DE | 2636634 | 2/1978 |
| DE | 3712089 | 10/1988 |
| DE | 4234016 | 10/1991 |
| DE | 4402319 | 8/1994 |
| DE | 19504111 | 8/1995 |

(Continued)

OTHER PUBLICATIONS

International Search Report for PCT/EP06/009240, mailed Jan. 4, 2007.

(Continued)

*Primary Examiner* — Arleen M Vazquez
*Assistant Examiner* — Son Le
(74) *Attorney, Agent, or Firm* — Wesley A. Nicolas; Marc A. Began; Reza Green

(57) ABSTRACT

The present invention relates to a contact free arrangement for determining an absolute position of a member adapted for setting an amount of medicament to be injected from a medication delivery device, or adapted for determining an amount of medicament injected from a medication delivery device. The arrangement according to the present invention comprises at least one track of reflector means, at least one emitter means, and at least one receiver means. The at least one emitter means and the at least one receiver means are adapted to electrically couple to a number of the reflector means. The electrical coupling may be capacitive or inductive. In addition, the present invention relates to a medication delivery device or a syringe having such arrangement.

24 Claims, 8 Drawing Sheets

(56) References Cited

U.S. PATENT DOCUMENTS

Figure 1:
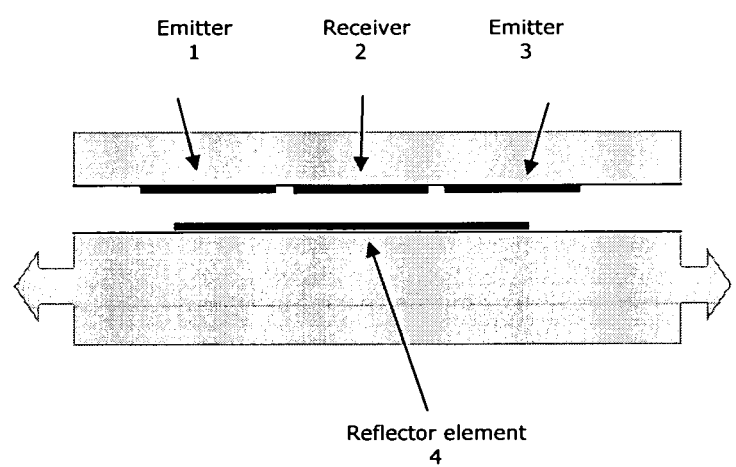

| | | |
|---|---|---|
| 3,916,157 A | 10/1975 | Roulette et al. |
| 3,998,513 A | 12/1976 | Kobayashi et al. |
| 4,179,212 A | 12/1979 | Lahr |
| 4,327,283 A | 4/1982 | Heyman et al. |
| 4,355,300 A | 10/1982 | Weber |
| 4,420,754 A | 12/1983 | Andermo |
| 4,449,042 A | 5/1984 | Hampson et al. |
| 4,476,149 A | 10/1984 | Poppe et al. |
| 4,476,381 A | 10/1984 | Rubin |
| 4,591,707 A | 5/1986 | Stenzel et al. |
| 4,625,101 A | 11/1986 | Hinks et al. |
| 4,636,786 A | 1/1987 | Haertling |
| 4,693,574 A | 9/1987 | Ohnuki et al. |
| 4,731,526 A | 3/1988 | Knoll et al. |
| 4,739,377 A | 4/1988 | Allen |
| 4,764,767 A * | 8/1988 | Ichikawa et al. ......... 340/870.31 |
| 4,810,867 A | 3/1989 | Speicher |
| 4,850,966 A | 7/1989 | Grau et al. |
| 4,853,521 A | 8/1989 | Claeys et al. |
| 4,857,716 A | 8/1989 | Gombrich et al. |
| 4,880,014 A | 11/1989 | Zarowitz et al. |
| 4,896,946 A | 1/1990 | Suzuki et al. |
| 4,930,263 A | 6/1990 | Rando |
| 4,950,246 A | 8/1990 | Muller |
| 4,959,056 A | 9/1990 | Dombrowski et al. |
| 4,978,335 A | 12/1990 | Arthur |
| 5,059,776 A | 10/1991 | Antes |
| 5,077,635 A | 12/1991 | Bollhagen et al. |
| 5,078,683 A | 1/1992 | Sancoff et al. |
| 5,091,798 A | 2/1992 | Hibino |
| 5,132,026 A | 7/1992 | Baluyot et al. |
| 5,153,827 A | 10/1992 | Courte et al. |
| 5,174,766 A | 12/1992 | Yoshizawa et al. |
| 5,176,502 A | 1/1993 | Sanderson et al. |
| 5,196,683 A | 3/1993 | Marom et al. |
| 5,239,307 A * | 8/1993 | Andermo ................. 340/870.37 |
| 5,271,527 A | 12/1993 | Haber et al. |
| 5,305,147 A | 4/1994 | Hasegawa et al. |
| 5,311,364 A | 5/1994 | Kanoshima et al. |
| 5,317,506 A | 5/1994 | Coutre et al. |
| 5,336,871 A | 8/1994 | Colgate |
| 5,379,131 A | 1/1995 | Yamazaki |
| 5,394,206 A | 2/1995 | Cocca |
| 5,403,616 A | 4/1995 | Hattori et al. |
| 5,418,649 A | 5/1995 | Igarashi |
| 5,422,472 A | 6/1995 | Tavislan et al. |
| 5,430,278 A | 7/1995 | Krieg et al. |
| 5,432,329 A | 7/1995 | Colgate et al. |
| 5,461,239 A | 10/1995 | Atherton |
| 5,523,560 A | 6/1996 | Manique et al. |
| 5,569,212 A | 10/1996 | Brown |
| 5,585,615 A | 12/1996 | Iwanami et al. |
| 5,593,390 A | 1/1997 | Castellano et al. |
| 5,628,309 A | 5/1997 | Brown |
| 5,637,854 A | 6/1997 | Thomas |
| 5,643,212 A | 7/1997 | Coutre et al. |
| 5,675,380 A | 10/1997 | Florent et al. |
| 5,686,725 A | 11/1997 | Maruyama et al. |
| 5,747,350 A | 5/1998 | Sattler |
| 5,757,521 A | 5/1998 | Walters et al. |
| 5,764,457 A | 6/1998 | Uhde et al. |
| 5,777,303 A | 7/1998 | Berney |
| 5,782,814 A | 7/1998 | Brown et al. |
| 5,786,584 A | 7/1998 | Button et al. |
| 5,791,880 A | 8/1998 | Wilson |
| 5,792,117 A | 8/1998 | Brown |
| 5,793,502 A | 8/1998 | Bianco et al. |
| 5,821,521 A | 10/1998 | Bridgelall et al. |
| 5,821,524 A | 10/1998 | Horlbeck et al. |
| 5,876,380 A | 3/1999 | Manganini et al. |
| 5,880,683 A | 3/1999 | Brandestini |
| 5,882,463 A | 3/1999 | Tompkin et al. |
| 5,895,369 A | 4/1999 | Flower |
| 5,902,990 A | 5/1999 | Stewart |
| 5,925,867 A | 7/1999 | Hagimoto |
| 5,954,700 A | 9/1999 | Kovelman |
| 5,986,585 A | 11/1999 | Pusch |
| 6,003,775 A | 12/1999 | Ackley |
| 6,019,745 A | 2/2000 | Gray |
| 6,047,892 A | 4/2000 | Schuessler et al. |
| 6,053,415 A | 4/2000 | Norwood |
| 6,068,615 A | 5/2000 | Brown et al. |
| 6,090,064 A | 7/2000 | Reilly et al. |
| 6,110,148 A | 8/2000 | Brown et al. |
| 6,110,152 A | 8/2000 | Kovelman |
| 6,168,080 B1 | 1/2001 | Verschuur et al. |
| 6,177,683 B1 | 1/2001 | Kolesar et al. |
| 6,202,929 B1 | 3/2001 | Verschuur et al. |
| 6,215,508 B1 | 4/2001 | Bryan et al. |
| 6,265,466 B1 | 7/2001 | Glatkowski et al. |
| 6,274,092 B1 | 8/2001 | Itoh |
| 6,303,929 B1 | 10/2001 | Oshima et al. |
| 6,329,813 B1 | 12/2001 | Andermo |
| 6,352,523 B1 | 3/2002 | Brown et al. |
| 6,372,293 B1 | 4/2002 | Mathus et al. |
| 6,435,175 B1 | 8/2002 | Stenzler |
| 6,475,192 B1 | 11/2002 | Reilly et al. |
| 6,533,183 B2 | 3/2003 | Aasmul et al. |
| 6,598,796 B2 | 7/2003 | Harrop |
| 6,652,812 B1 | 11/2003 | Vartiainen et al. |
| 6,669,090 B2 | 12/2003 | Eilersen |
| 6,700,391 B2 | 3/2004 | Strack et al. |
| 6,813,868 B2 | 11/2004 | Baldwin et al. |
| 6,854,653 B2 | 2/2005 | Eilersen |
| 6,954,700 B2 | 10/2005 | Higashida et al. |
| 6,957,522 B2 | 10/2005 | Baldwin et al. |
| 6,976,349 B2 | 12/2005 | Baldwin et al. |
| 6,994,261 B2 | 2/2006 | Eilersen |
| 7,018,363 B2 | 3/2006 | Cowan et al. |
| 7,041,941 B2 | 5/2006 | Faries et al. |
| 7,061,831 B2 | 6/2006 | De La Huerga |
| 7,074,209 B2 | 7/2006 | Evans et al. |
| 7,077,332 B2 | 7/2006 | Verschuur et al. |
| 7,104,973 B2 | 9/2006 | Woolston et al. |
| 7,108,184 B2 | 9/2006 | Mase et al. |
| 7,164,133 B2 | 1/2007 | Hjertman et al. |
| 7,462,166 B2 | 12/2008 | Cowan et al. |
| 7,511,480 B2 | 3/2009 | Steffen |
| 7,704,231 B2 | 4/2010 | Pongpairochana et al. |
| 8,140,349 B2 | 3/2012 | Hanson et al. |
| 2001/0001472 A1 | 5/2001 | Sano et al. |
| 2001/0013544 A1 | 8/2001 | Rathus et al. |
| 2001/0015202 A1 | 8/2001 | Miller |
| 2001/0034506 A1 | 10/2001 | Hirschman et al. |
| 2002/0000471 A1 | 1/2002 | Aasmul et al. |
| 2002/0012176 A1 | 1/2002 | Ning |
| 2002/0020654 A1 | 2/2002 | Eilersen |
| 2002/0022821 A1 | 2/2002 | Eilersen |
| 2002/0063156 A1 | 5/2002 | Marchand |
| 2002/0106309 A1 | 8/2002 | Mathus et al. |
| 2002/0117549 A1 | 8/2002 | Lee |
| 2002/0117579 A1 | 8/2002 | Kotoulas et al. |
| 2002/0123078 A1 | 9/2002 | Seul et al. |
| 2002/0177237 A1* | 11/2002 | Shvets et al. .................. 436/180 |
| 2003/0015590 A1 | 1/2003 | Chen |
| 2003/0034439 A1* | 2/2003 | Reime et al. .................. 250/221 |
| 2003/0039590 A1 | 2/2003 | Lodge |
| 2003/0116630 A1 | 6/2003 | Carey et al. |
| 2003/0143614 A1 | 7/2003 | Drmanac |
| 2003/0205625 A1 | 11/2003 | Eilersen |
| 2003/0233041 A1* | 12/2003 | Yaksh et al. .................. 600/409 |
| 2003/0233069 A1 | 12/2003 | Gillespie et al. |
| 2004/0008853 A1 | 1/2004 | Pelrine et al. |
| 2004/0024368 A1 | 2/2004 | Broselow |
| 2004/0046032 A1 | 3/2004 | Urano et al. |
| 2004/0051368 A1 | 3/2004 | Caputo et al. |
| 2004/0082918 A1 | 4/2004 | Evans et al. |
| 2004/0141426 A1 | 7/2004 | Kawasaki et al. |
| 2004/0155113 A1 | 8/2004 | Urano et al. |
| 2004/0178255 A1 | 9/2004 | Eich et al. |
| 2004/0200558 A1 | 10/2004 | Stevens et al. |
| 2004/0207385 A1* | 10/2004 | Gafner et al. ............. 324/76.11 |
| 2004/0210199 A1* | 10/2004 | Atterbury et al. ............. 604/224 |
| 2005/0006472 A1 | 1/2005 | Verschuur et al. |

(56) References Cited

U.S. PATENT DOCUMENTS

| | | |
|---|---|---|
| 2005/0035207 A1 | 2/2005 | Philyaw et al. |
| 2005/0060059 A1 | 3/2005 | Klein et al. |
| 2005/0116033 A1 | 6/2005 | Moore |
| 2005/0156318 A1 | 7/2005 | Douglas |
| 2005/0182360 A1 | 8/2005 | Yeandel et al. |
| 2005/0236603 A1 | 10/2005 | Faris |
| 2005/0283116 A1 | 12/2005 | Eakins et al. |
| 2006/0097877 A1 | 5/2006 | Baba et al. |
| 2006/0118612 A1 | 6/2006 | Christoffersen et al. |
| 2006/0125491 A1 | 6/2006 | Grishin et al. |
| 2006/0129104 A1 | 6/2006 | Cowan et al. |
| 2006/0138233 A1 | 6/2006 | Kemppainen et al. |
| 2006/0164002 A1 | 7/2006 | O'Brien et al. |
| 2006/0170981 A1 | 8/2006 | Ricks et al. |
| 2006/0175427 A1 | 8/2006 | Jonientz et al. |
| 2006/0176267 A1 | 8/2006 | Honeyman et al. |
| 2006/0224123 A1 | 10/2006 | Friedli et al. |
| 2006/0226238 A1 | 10/2006 | Salib et al. |
| 2006/0243804 A1 | 11/2006 | Christoffersen et al. |
| 2007/0080234 A1 | 4/2007 | Domoy |
| 2007/0239116 A1 | 10/2007 | Follman et al. |
| 2008/0015510 A1 | 1/2008 | Sandoz et al. |
| 2008/0269664 A1 | 10/2008 | Trovato et al. |
| 2009/0088701 A1 | 4/2009 | Larsen |

FOREIGN PATENT DOCUMENTS

| | | |
|---|---|---|
| DE | 19637967 | 9/1996 |
| DE | 19814687 | 2/1999 |
| DE | 10035192 | 10/2001 |
| EP | 235691 | 9/1987 |
| EP | 248165 | 12/1987 |
| EP | 336778 | 10/1989 |
| EP | 364010 | 4/1990 |
| EP | 398717 | 11/1990 |
| EP | 402553 | 12/1990 |
| EP | 492954 | 7/1992 |
| EP | 573129 | 12/1993 |
| EP | 588427 | 3/1994 |
| EP | 626660 | 11/1994 |
| EP | 685810 | 12/1995 |
| EP | 690457 | 1/1996 |
| EP | 716290 | 6/1996 |
| EP | 833273 | 4/1998 |
| EP | 833278 | 4/1998 |
| EP | 911859 | 4/1999 |
| EP | 1095668 A1 | 5/2001 |
| EP | 1142643 | 10/2001 |
| EP | 1143643 | 10/2001 |
| EP | 1193641 | 4/2002 |
| EP | 1246127 | 10/2002 |
| EP | 1462134 | 9/2004 |
| EP | 1503185 | 2/2005 |
| FR | 2771111 | 5/1999 |
| GB | 2088163 | 6/1982 |
| GB | 2159007 | 11/1985 |
| GB | 2216259 | 10/1989 |
| GB | 2287551 | 9/1995 |
| GB | 2309801 | 8/1997 |
| GB | 2336927 | 11/1999 |
| GB | 2341965 | 3/2000 |
| JP | 56-094475 | 7/1981 |
| JP | 59-131917 A | 7/1984 |
| JP | 63-100303 A | 5/1988 |
| JP | 2-85370 | 3/1990 |
| JP | 2-188702 | 7/1990 |
| JP | 2-250083 | 10/1990 |
| JP | 3-27037 A | 2/1991 |
| JP | 4-222084 A | 8/1992 |
| JP | 4-233680 A | 8/1992 |
| JP | 4-233684 A | 8/1992 |
| JP | 5006449 | 1/1993 |
| JP | 5-500917 | 2/1993 |
| JP | 5-314296 | 11/1993 |
| JP | 6-163027 | 6/1994 |
| JP | 06-171194 | 6/1994 |
| JP | 6-333102 | 12/1994 |
| JP | 7-098752 | 4/1995 |
| JP | 7-271890 | 10/1995 |
| JP | 8-106648 | 4/1996 |
| JP | 8-118864 | 5/1996 |
| JP | 8-179475 | 7/1996 |
| JP | 8-220994 | 8/1996 |
| JP | 8-262980 | 10/1996 |
| JP | 9-16703 | 1/1997 |
| JP | 9-034361 | 2/1997 |
| JP | 9-091364 | 4/1997 |
| JP | 9-192220 | 7/1997 |
| JP | 9-223181 | 8/1997 |
| JP | 9-274637 | 10/1997 |
| JP | 10-105635 | 4/1998 |
| JP | 10-268777 | 10/1998 |
| JP | 11-135172 | 5/1999 |
| JP | 11-162591 | 6/1999 |
| JP | 11-180079 | 7/1999 |
| JP | 11-276583 | 10/1999 |
| JP | 11-316877 | 11/1999 |
| JP | 2000-040119 | 2/2000 |
| JP | 2000-272191 | 10/2000 |
| JP | 2001-043301 | 2/2001 |
| JP | 2001-075480 | 3/2001 |
| JP | 2002-082120 | 3/2002 |
| JP | 2002-517737 | 6/2002 |
| JP | 4-233624 B2 | 12/2008 |
| WO | WO 91/04759 | 4/1991 |
| WO | WO 92/17231 | 10/1992 |
| WO | WO 93/12828 | 7/1993 |
| WO | WO 94/08647 | 4/1994 |
| WO | WO 94/12235 | 6/1994 |
| WO | 94/15120 | 7/1994 |
| WO | WO 95/24317 | 9/1995 |
| WO | WO 95/28190 | 10/1995 |
| WO | WO 99/60533 | 11/1999 |
| WO | WO 99/65548 | 12/1999 |
| WO | WO 00/42678 | 7/2000 |
| WO | WO 01/22348 | 3/2001 |
| WO | WO 01/54055 | 7/2001 |
| WO | WO 01/62322 | 8/2001 |
| WO | WO 01/70304 | 9/2001 |
| WO | WO 01/84542 | 11/2001 |
| WO | 0195959 | 12/2001 |
| WO | WO 02/11792 | 2/2002 |
| WO | WO 02/13133 | 2/2002 |
| WO | WO 02/092153 | 11/2002 |
| WO | WO 02/095675 | 11/2002 |
| WO | 03/011370 A2 | 2/2003 |
| WO | 03/011372 A2 | 2/2003 |
| WO | 03/011373 A1 | 2/2003 |
| WO | 03/011374 A1 | 2/2003 |
| WO | 03011371 A2 | 2/2003 |
| WO | WO 03/017915 | 3/2003 |
| WO | WO 03/020598 | 3/2003 |
| WO | WO 03/038738 | 5/2003 |
| WO | WO 2004/084795 | 10/2004 |
| WO | WO 2004/097715 | 11/2004 |
| WO | WO 2005/075010 | 8/2005 |
| WO | WO 2005/089835 | 9/2005 |
| WO | 2005/110387 | 11/2005 |
| WO | 2006/113521 | 10/2006 |
| WO | 2006/120182 | 11/2006 |
| WO | WO 2007/039148 | 4/2007 |
| WO | WO 2007/107562 | 9/2007 |
| WO | WO 2007/116090 A1 | 10/2007 |
| WO | WO 2007/122253 A1 | 11/2007 |
| WO | WO 2009/015933 | 2/2009 |

OTHER PUBLICATIONS

CN 1051152 English Abstract, Sep. 15, 1993.
CN 1013704 English Abstract, Aug. 28, 1991.
DE 19814687 Machine Translation, Feb. 18, 1999.
DE 19637967 English Abstract, Oct. 30, 1997, DE 19637967 previously cited.

(56) References Cited

OTHER PUBLICATIONS

DE 19504111 Machine Translation, Aug. 10, 1995.
DE 10035192 Machine Translation, Oct. 11, 2001, DE 10035192 previously cited.
DE 4234016 English Abstract, Apr. 15, 1993, DE 423016 previously cited.
DE 3712089 English Abstract, Oct. 27, 1988.
DE 2636634 English Abstract, Feb. 16, 1978.
FR 2771111 Machine Translation, May 21, 1999.
JP 2002-517737 Machine Translation, Jun. 18, 2002.
JP 2002-082120 English Abstract, Mar. 22, 2002.
JP 2001-075480 English Abstract, Mar. 23, 2001.
JP 2001-043301 Machine Translation, Feb. 16, 2001.
JP 2000-040119 Machine Translation, Feb. 8, 2000.
JP 2000-272191 Machine Translation, Oct. 3, 2000.
JP 11-316877 Machine Translation Nov. 16, 1999.
JP 11-180079 Machine Translation, Jul. 6, 1999.
JP 11-162591 Machine Translation, Jun. 18, 1999.
JP 11-135172 Machine Translation, May 21, 1999.
JP 10-268777 Machine Translation, Oct. 9, 1998.
JP 10-105635 Machine Translation, Apr. 24, 1998.
JP 9-274637 Machine Translation, Oct. 21, 1997.
JP 9-223181 Machine Translation, Aug. 26, 1997.
JP 9-192220 Machine Translation, Jul. 29, 1997.
JP 9-091364 Machine Translation, Apr. 4, 1997.
JP 9-034361 Machine Translation, Feb. 7, 1997.
JP 9-16703 Machine Translation, Jan. 17, 1997.
JP 8-262980 Machine Translation, Oct. 11, 1996.
JP 8-220994 Machine Translation, Aug. 30, 1996.
JP 8-179475 Machine Translation, Jul. 12, 1996.
JP 8-118864 Machine Translation, May 14, 1996.
JP 8-106648 Machine Translation, Apr. 23, 1996.
JP 7-271890 Machine Translation, Oct. 20 1995.
JP 7-098752 Machine Translation, Apr. 11, 1995.
JP 6-333102 Machine Translation, Dec. 2, 1994.
JP 63-100303A English Abstract, May 2, 1988.
JP 6-163027 Machine Translation, Jun. 10, 1994.
JP 59-131917 English Abstract, Jul. 28, 1984.
JP 5-314296 Machine Translation, Nov. 26, 1993.
JP 5-500917 English Abstract, Feb. 25, 1993.
JP 4-233684A English Abstract, Aug. 21, 1992.
JP 4-233680A English Abstract, Aug. 21, 1992.
JP 4-233624B2 Machine Translation, Dec. 19, 2008.
JP 4-222084 English Abstract, Aug. 12, 1992.
JP 3-27037A English Abstract, Feb. 5, 1991.
JP 2-250083 English Abstract, Oct. 5, 1990.
JP 2-188702 English Abstract, Jul. 24, 1990.
JP 2-85370 English Abstract, Mar. 26, 1990.
WO 01/22348 English Abstract, Mar. 29, 2001.
Non-Final Office Action mailed Jan. 4, 2008 in U.S. Appl. No. 11/396,889, filed Apr. 3, 2006 by Christoffersen et al.
Notice of Allowance mailed Sep. 17, 2009 in U.S. Appl. No. 11/296,991, filed Dec. 8, 2005 by Eilersen et al.
Notice of Allowance mailed Apr. 30, 2009 in U.S. Appl. No. 11/296,991, filed Dec. 8, 2005 by Eilersen et al.
Non-Final Office Action mailed Oct. 14, 2008 in U.S. Appl. No. 11/296,991, filed Dec. 8, 2005 by Eilersen et al.
Corrected Notice of Allowance mailed Jun. 19, 2009 in U.S. Appl. No. 11/232,469, filed Sep. 19, 2005 by Christoffersen et al.
Notice of Allowance mailed Jun. 8, 2009 in U.S. Appl. No. 11/232,469, filed Sep. 19, 2005 by Christoffersen et al.
Non-Final Office Action mailed Dec. 17, 2008 in U.S. Appl. No. 11/232,469, filed Sep. 19, 2005 by Christoffersen et al.
Final Office Action mailed Jul. 2, 2008 in U.S. Appl. No. 11/232,469, filed Sep. 19, 2005 by Christoffersen et al.
Non-Final Office Action mailed Jan. 3, 2008 in U.S. Appl. No. 11/232,469, filed Sep. 19, 2005 by Christoffersen et al.
Non-Final Office Action mailed Jun. 19, 2007 in U.S. Appl. No. 11/232,469, filed Sep. 19, 2005 by Christoffersen et al.
Non-Final Office Action mailed Oct. 23, 2003 in U.S. Appl. No. 10/463,915, filed Jun. 18, 2003 by Eilersen et al.
Non-Final Office Action mailed Apr. 15, 2004 in U.S. Appl. No. 10/463,915, filed Jun. 18, 2003 by Eilersen et al.
Notice of Allowance mailed Aug. 16, 2004 in U.S. Appl. No. 10/463,915, filed Jun. 18, 2003 by Eilersen et al.
Notice of Allowance mailed Aug. 13, 2003 in U.S. Appl. No. 09/925,995, filed Aug. 9, 2001 by Eilersen et al.
Non-Final Office Action mailed Nov. 12, 2002 in U.S. Appl. No. 09/925,995, filed Aug. 9, 2001 by Eilersen et al.
Notice of Allowance mailed Aug. 11, 2005 in U.S. Appl. No. 09/925,792, filed Aug. 9, 2001 by Eilersen et al.
Non-Final Office Action mailed Apr. 4, 2005 in U.S. Appl. No. 09/925,792, filed Aug. 9, 2001 by Eilersen et al.
Notice of Allowance mailed Oct. 8, 2002 in U.S. Appl. No. 09/846,799, filed May 1, 2001 by Aasmul et al.
Non-Final Office Action mailed May 8, 2002 in U.S. Appl. No. 09/846,799, filed May 1, 2001 by Aasmul et al.
International Search Report for PCT/EP2007/054069, mailed Sep. 17, 2007.
International Search Report for PCT/EP2007/053558, mailed Jul. 23, 2007.
English Language Abstract of German Patent No. 4402319, published Aug. 4, 1994, obtained from espacenet.com database.
JP 11-276583 English Abstract Oct. 12, 1999.
JP 06-171194 English Abstract Jun. 21, 1994.
JP 56-094475 English Abstract Jul. 30, 1981.
JP 5006449 English Abstract Jan. 14, 1993.
Non-Final Office Action Mailed Oct. 30, 2010 in U.S. Appl. No. 11/912,347, filed Oct. 23, 2007; First Named Inventor: Preben Mikael Nielsen.
Final Office Action Mailed Apr. 15, 2011 in U.S. Appl. No. 11/912,347, filed Oct. 23, 2007; First Named Inventor: Preben Mikael Nielsen.

* cited by examiner

DEVICE AND METHOD FOR CONTACT FREE ABSOLUTE POSITION DETERMINATION

CROSS-REFERENCE TO RELATED APPLICATIONS

This application is a 35 U.S.C. §371 national stage application of International Patent Application PCT/EP2006/009240 (published as WO 2007/039148), filed Sep. 22, 2006, which claimed priority of European Patent Application No. 05020657.2, filed Sep. 22, 2005; this application further claims priority under 35 U.S.C. §119 of U.S. Provisional Application 60/720,593, filed Sep. 25, 2005.

FIELD OF THE INVENTION

The present invention relates to a contact free arrangement for determining an absolute position of a member adapted for setting an amount of medicament to be injected from a medication delivery device, or for determining an amount of medicament injected from a medication delivery device. The arrangement according to the present invention comprises at least one track of reflector means, at least one emitter means, and at least one receiver means. The at least one emitter means and the at least one receiver means are adapted to electrically couple to a number of the reflector means. The electrical coupling may be capacitive or inductive. In addition, the present invention relates to a medication delivery device or a syringe having such arrangement incorporated therein.

BACKGROUND OF THE INVENTION

U.S. Pat. No. 4,420,754 discloses a system for measuring the relative movement between two elements, such as the scale and slide of a hand-held measuring instrument. The system includes the provision of a number of groups of supply electrodes on the slide, each of the electrodes in each group being supplied from a respective one of a multiple number of output signals from a signal generator so that all of the supply electrodes are furnished with voltages according to a cyclic pattern, the slide also having at least one receiving electrode which feeds a signal processing unit. The scale is provided with an electronic pattern comprising internally galvanically connected parts, one being a detecting part, located close to the area where the supply electrodes of the slide are moved, the other of the two parts being a transferring part which is located close to the area where the receiving electrode of the slide is moved. The movement of the slide along the scale generates a signal from the receiving electrode which is derived from the signals from at least two adjacent supply electrodes and the position of the slide is determined by a signal processing unit which identifies the amplitude ratio of the received signals.

U.S. Pat. No. 6,329,813 discloses an inductive absolute position sensor applying at least one magnetic field generator that generates a first changing magnetic flux in a first flux region. A plurality of coupling loops have a first plurality of coupling loop portions spaced at an interval related to a first wavelength along a measuring axis and a second plurality of coupling loop portions spaced at an interval related to a second wavelength along a measuring axis. One of the first plurality of coupling loop portions and the second plurality of coupling loop portions are inductively coupled to a first changing magnetic flux from a transmitter winding in a first flux region to generate a second changing magnetic flux outside the first flux region in the other of the first plurality of coupling loop portions and the second plurality of coupling loop portions. A magnetic flux sensor is positioned outside the first flux region and is responsive to the second changing magnetic flux to generate a position-dependent output signal. The output signal varies at the first or second wavelength of the corresponding other of the first plurality of coupling loop portions and the second plurality of coupling loop portions that generates the second changing magnetic flux.

The arrangements suggested in both U.S. Pat. No. 4,420,754 and U.S. Pat. No. 6,329,813 are adapted for determining linear translations between two objects.

US 2004/0207385 relates to a device for detecting the angular position of a rotatably mounted rotor relative to a stationary stator, wherein at least one electrode is arranged on the rotor and at least one electrode is arranged on the stator in such a way that the electrodes at least partially overlap in at least one rotational position of the rotor relative to the stator. US 2004/0207385 further relates to a method for measuring the rotational position of a rotor comprising at least one rotor electrode relative to a stator comprising at least one stator electrode, wherein the rotational position is detected using a capacitive coupling between the rotor electrode and the stator electrode.

US 2004/0207385 relates to the determining of angular positions between two objects such as between a rotatably mounted rotor and a stationary stator. It is a disadvantage of the arrangement suggested in US 2004/0207385 that the emitter and receiver electrodes are positioned in a manner where they take up an unnecessary amount of space. For compact systems the solution suggested by US 2004/0207385 is not applicable.

Figure 8:
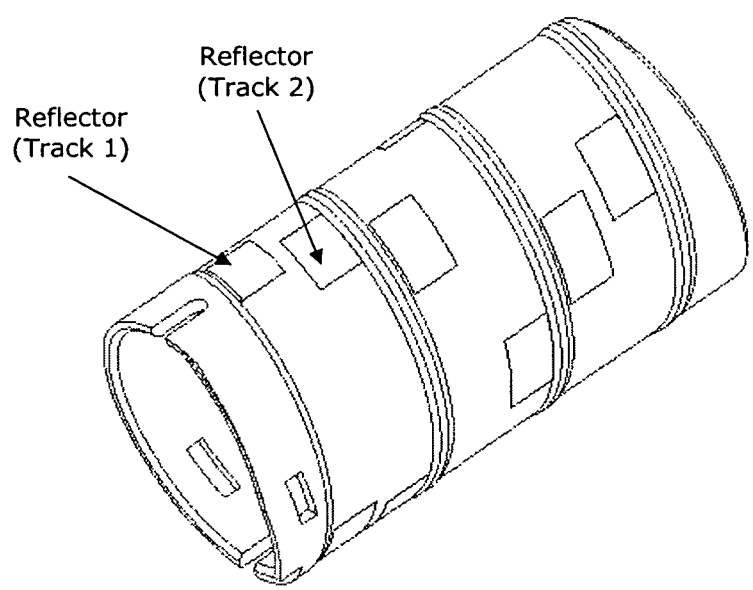

Furthermore, the arrangement suggested in US 2004/0207385 is not adapted for contact free and absolute position determination. As depicted in FIGS. 8 and 9 of US 2004/0207385 and the corresponding text in paragraphs 0053 and 0054 additional components such as force sensors or electrical resistors are required if absolute measurements are to be performed. Thus, it is a disadvantage of the arrangement suggested in 2004/0207385 that absolute measurements cannot be performed in a contact free mode of operation. If absolute, and not only relative measurement are to be performed, contact requiring elements, such as force sensors and electrical resistors, are required. Thus, it is a disadvantage of the arrangement suggested in US 2004/0207385 that only relative position measurements between rotor and stator can be performed in a contact free mode of operation.

It is a further disadvantage of the arrangement suggested in US 2004/0207385 that the rotor is only allowed to the rotated one revolution if its position needs to be tracked. Thus, if the rotor of US 2004/0207385 is rotated more than one revolution, the signals exclusively obtainable from the electrodes no longer provides an unambiguously determination of the angular position relative to the stator. Finally, the arrangement suggested in US 2004/0207385 suffers from the significant drawback that the capacitance used for determining the angular position of the rotor relative to the stator involves determining a capacitance between at least one rotor electrode and at least one stator electrode. In order to determine this capacitance electrical access needs to be provided to the rotor which is a rotatably mounted element. Providing such electrical access to a rotatably mounted member is certainly not a simple and straight forward process.

It is an object of the present invention to provide a compact and contact free arrangement for determining the absolute angular position of a dose setting member of a medication delivery device or for determining an actual dose of medicament expelled from a medication delivery device. The amount of medicament expelled from the medication delivery device is determined from an absolute angular position of a dose setting member. By absolute angular position is meant that the absolute position of the dose setting member relative to a housing of the medication delivery device is always known.

SUMMARY OF THE INVENTION

The above-mentioned object is complied with by providing, in a first aspect, a contact free arrangement for determining an absolute angular position of a moveably mounted member, such as a rotatably mounted dose setting member, in a medication delivery device, the arrangement comprising at least one track of reflector means,
at least one emitter means, the at least one emitter means being adapted to electrically couple to a number of the reflector means, and
at least one receiver means, the at least one receiver means being adapted to electrically couple to a number of the reflector means wherein the at least one track of reflector means is moveably arranged relative to the at least one emitter means and the at least one receiver means in such a manner that there is provided an unambiguously determinable electrical parameter, such as a capacitance, to each of a number of discrete positions of the at least one track of reflector means relative to the at least one emitter means and the at least one receiver means.

Thus, the arrangement according to the present invention may be applied to determine a dose of medicament to be injected from a medication delivery device by determining the angular position of a dose setting member. Alternatively or in addition, the arrangement according to the present invention may be applied to determine an amount of medicament injected from the medication delivery device by determining the shift in angular position of a dose setting member, when said dose setting member is rotated from a set position to an initial position.

At least part of the at least one track of reflector means may form a helical, circular or linear path. The reflector means may have a floating electrical potential meaning that the reflector means may not be electrically connected to a specific electrical potential. The at least one track of reflector means may be arranged on the rotatably mounted member of the medication delivery device, such as on a dose indicator barrel. Obviously, in case the at least one track of reflector means is arranged along a substantially helical path the arrangement according to the first aspect of the present invention must be capable of determining the absolute position of the rotatably mounted member over an angle of rotation exceeding one revolution.

In one embodiment of the present invention a single track of reflector means is provided. This single track of reflector means may comprise a helical-shaped row of electrically conducting members arranged on the moveably mounted member of the medication delivery device. The dimensions, such as the length, of the electrically conducting members forming the track may vary monotonically along an axial direction of the row of electrically conducting members.

In a second embodiment, a first and a second track of reflector means may be provided. The first and second tracks of reflector means may be arranged in a substantially parallel manner. As with the first embodiment, the first track of reflector means may comprise a helical-shaped row of electrically conducting members arranged on the moveably mounted member of the medication delivery device, the electrically conducting members of the first track defining a first period.

The second track of reflector means may comprise a helical-shaped row of electrically conducting members arranged on the moveably mounted member of the medication delivery device, the electrically conducting members of the second track defining a second period. Preferably, the first period may be different from the second period.

Contrary to the reflectors, which are arranged on a rotating part of the medication delivery device, such as on the dose indicator barrel, the at least one emitter may be arranged on a non-rotatably mounted part of the medication delivery device, such as on an inner surface of the housing of the medication delivery device. Similarly, the at least one receiver may be arranged on a non-rotatably mounted part of the medication delivery device. Again, this could be on an inner surface of the housing.

The first and second tracks of reflector means may each comprise an essentially unbroken path of an electrically conducting material. The width of said essentially unbroken paths of electrically conducting material may vary along the axial directions of the tracks. Thus, the first track may have a narrow width at its starting point and a wider width at its end point. Oppositely, the second track may have a significant width at its starting point and a narrower width at end point.

The at least one emitter and a number of the reflector means may form a capacitor in combination. Similarly, the at least one receiver and a number of the reflector means may form a capacitor in combination.

Alternatively, the at least one emitter and a number of the reflector means may be adapted to couple in an inductive manner. Similarly, the at least one receiver and a number of the reflector means may be adapted to couple in an inductive manner. In order to achieve such an inductive coupling, the at least one emitter and the at least one receiver may comprise a coil adapted for generating and receiving a magnetic field, respectively, whereas a number of the reflector means may be configured so as to support eddy currents induced by the at least one emitter.

In a preferred embodiment two emitter means and one receiver means are provided for each track. The two emitter means and the one receiver means may be arranged along a substantially straight line, wherein the receiver means is arranged between the two emitter means.

The arrangement may further comprise processor means for processing a signal or signals from the at least one receiver means, and generator means for generating a signal or signals and providing such signal(s) to the at least one emitter means. Such processor and generator means may be of the conventional and well known type.

In a second aspect, the present invention relates to a medication delivery device or a syringe comprising an arrangement according to the first aspect of the present invention.

In a third aspect, the present invention relates to a contact free method for determining an absolute angular position of a moveably mounted member, such as a rotatably mounted dose setting member, in a medication delivery device, the method comprising the steps of providing at least one track of reflector means,
providing an electrical signal to at least one emitter means, the at least one emitter means being electrically coupled to a number of the reflector means, and
receiving an electrical signal from at least one receiver means, the at least one receiver means being electrically coupled to a number of the reflector means wherein the at least one track of reflector means is moveably arranged relative to the at least one emitter means and the at least one receiver means in such a manner that there is provided an unambiguously determinable electrical parameter, such as a capacitance, to each of a number of discrete positions of the at least one track of reflector means relative to the at least one emitter means and the at least one receiver means.

A first electrical signal may be provided to a first emitter, whereas a second electrical signal may be provided to a second emitter, the first and second electrical signals being approximately 180 degrees out of phase. The electrical signals provided to the first and second emitters may oscillate with a frequency within the range 50 kHz-150 kHz, such as within the range 90 kHz-110 kHz. The frequency of the first electrical signal may be frequency shifted 8-10% relative to the frequency of the second electrical signal.

In a third aspect, the present invention relates to a contact free arrangement in a medication delivery device for determining an absolute position of a first member moveably mounted relative to a second member, the first member being restricted for movement between a first end position and a second end position, the arrangement comprising at least one track of reflector means associated with the first member, at least one emitter means associated with the second member, the at least one emitter means being adapted to electrically couple to a number of the reflector means, and at least one receiver means associated with the second member, the at least one receiver means being adapted to electrically couple to a number of the reflector means wherein the first member is arranged relative to the second member in such a manner that there is provided an unambiguously determinable electrical parameter, such as a capacitance, to each respective position of the first member relative to the second member.

Similar to the first aspect of the present invention, the arrangement according to the present invention may be applied to determine a dose of medicament to be injected from a medication delivery device by determining the angular position of a dose setting member. Alternatively or in addition, the arrangement according to the present invention may be applied to determine an amount of medicament injected from the medication delivery device by determining the shift in angular position of a dose setting member, when said dose setting member is rotated from a set position to an initial position.

At least part of the at least one track of reflector means may form a helical, circular or linear path. The reflector means may have a floating electrical potential meaning that the reflector means may not be electrically connected to a specific electrical potential. The at least one track of reflector means may be arranged on the first member, such as a rotatably mounted member, of the medication delivery device. The rotatably mounted member may be a dose indicator barrel. Obviously, in case the at least one track of reflector means is arranged along a substantially helical path the arrangement according to this aspect of the present invention must be capable of determining the absolute position of the rotatably mounted member over an angle of rotation exceeding one revolution.

In one embodiment of the third aspect of the present invention a single track of reflector means is provided. This single track of reflector means may comprise a helical-shaped row of electrically conducting members arranged on the first member of the medication delivery device. The dimensions, such as the length, of the electrically conducting members forming the track may vary monotonically along an axial direction of the row of electrically conducting members.

In another embodiment of the third aspect, a first and a second track of reflector means may be provided. The first and second tracks of reflector means may be arranged in a substantially parallel manner. As with the first embodiment, the first track of reflector means may comprise a helical-shaped row of electrically conducting members arranged on the first member of the medication delivery device, the electrically conducting members of the first track defining a first period. The second track of reflector means may comprise a helical-shaped row of electrically conducting members arranged on the first member of the medication delivery device, the electrically conducting members of the second track defining a second period. Preferably, the first period may be different from the second period.

Contrary to the reflectors, which are arranged on a rotating part of the medication delivery device, such as on the dose indicator barrel, the at least one emitter may be arranged on a non-rotatably mounted part of the medication delivery device, such as on an inner surface of the housing of the medication delivery device. Similarly, the at least one receiver may be arranged on a non-rotatably mounted part of the medication delivery device. Again, this could be on an inner surface of the housing.

The first and second tracks of reflector means may each comprise an essentially unbroken path of an electrically conducting material. The width of said essentially unbroken paths of electrically conducting material may vary along the axial directions of the tracks. Thus, the first track may have a narrow width at its starting point and a wider width at its end point. Oppositely, the second track may have a significant width at its starting point and a narrower width at end point.

The at least one emitter and a number of the reflector means may form a capacitor in combination. Similarly, the at least one receiver and a number of the reflector means may form a capacitor in combination.

Alternatively, the at least one emitter and a number of the reflector means may be adapted to couple in an inductive manner. Similarly, the at least one receiver and a number of the reflector means may be adapted to couple in an inductive manner. In order to achieve such an inductive coupling, the at least one emitter and the at least one receiver may comprise a coil adapted for generating and receiving a magnetic field, respectively, whereas a number of the reflector means may be configured so as to support eddy currents induced by the at least one emitter.

In a preferred embodiment two emitter means and one receiver means are provided for each track. The two emitter means and the one receiver means may be arranged along a substantially straight line, wherein the receiver means is arranged between the two emitter means.

The arrangement may further comprise processor means for processing a signal or signals from the at least one receiver means, and generator means for generating a signal or signals and providing such signal(s) to the at least one emitter means. Such processor and generator means may be of the conventional and well known type.

In a fourth aspect, the present invention relates to a contact free method for determining an absolute position of a first member moveably mounted relative to a second member in a medication delivery device, the first member being restricted for movement between a first end position and a second end position, the method comprising the steps of providing at least one track of reflector means associated with the first member, providing an electrical signal to at least one emitter means associated with the second member, the at least one emitter means being electrically coupled to a number of the reflector means, and receiving an electrical signal from at least one receiver means associated with the second member, the at least one receiver means being electrically coupled to a number of the reflector means wherein the first member is arranged relative to the second member in such a manner that there is provided an unambiguously determinable electrical parameter, such as a capacitance, to each respective position of the first member relative to the second member.

As with the second aspect of the present invention, a first electrical signal may be provided to a first emitter, whereas a second electrical signal may be provided to a second emitter, the first and second electrical signals being approximately 180 degrees out of phase. The electrical signals provided to the first and second emitters may oscillate with a frequency within the range 50 kHz-150 kHz, such as within the range 90 kHz-110 kHz. The frequency of the first electrical signal may be frequency shifted 8-10% relative to the frequency of the second electrical signal.

BRIEF DESCRIPTION OF THE INVENTION

Figure 2:
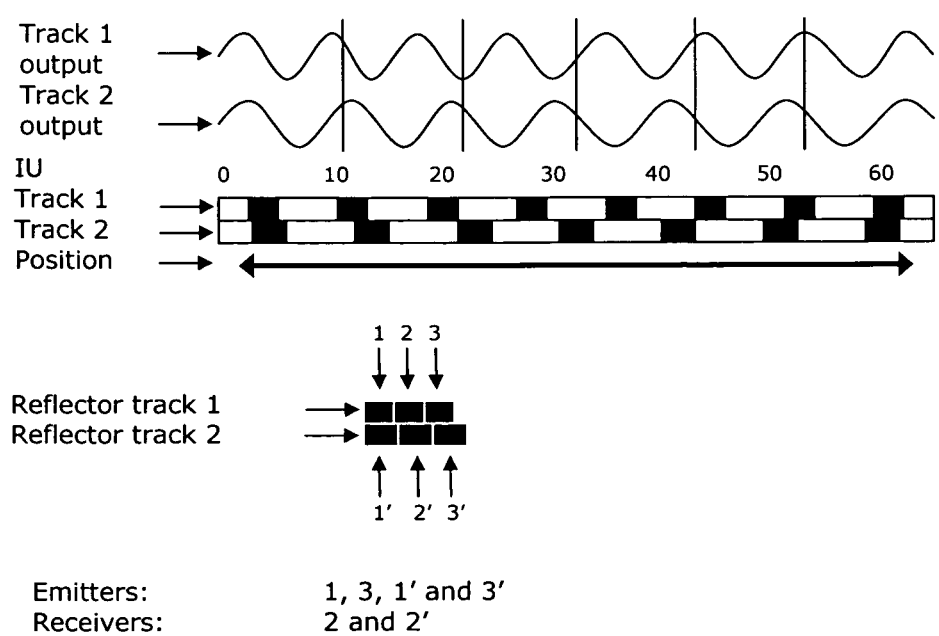
Figure 3:
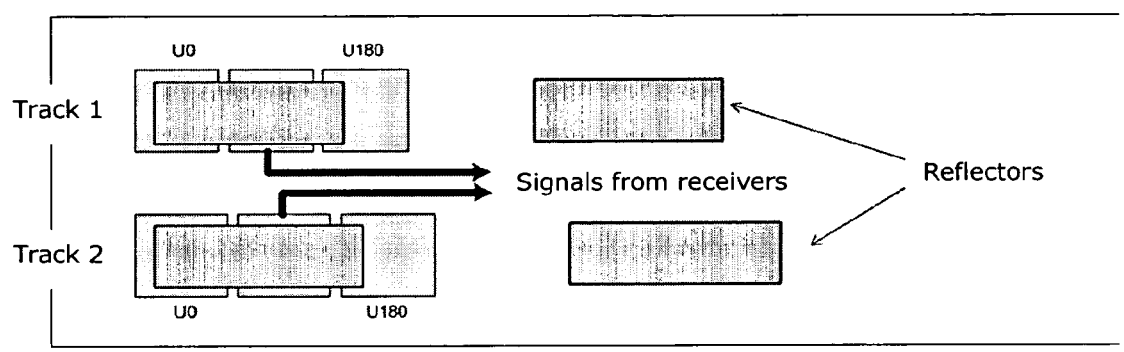
Figure 4:
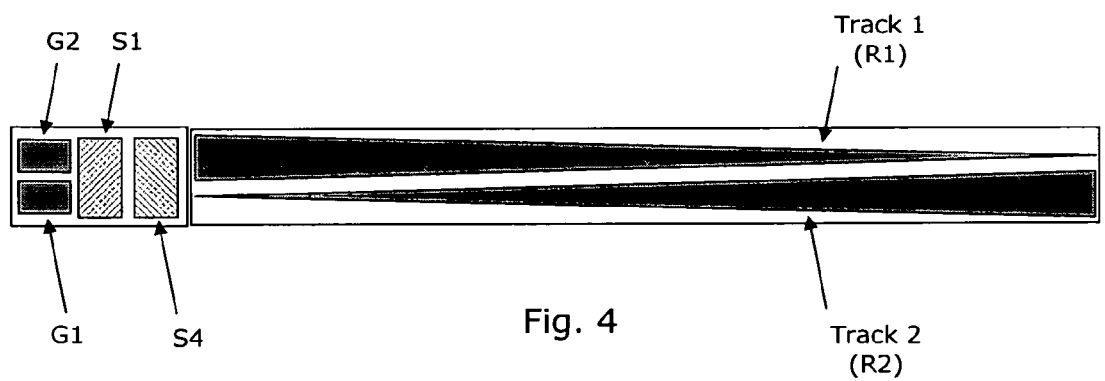
Figure 5:
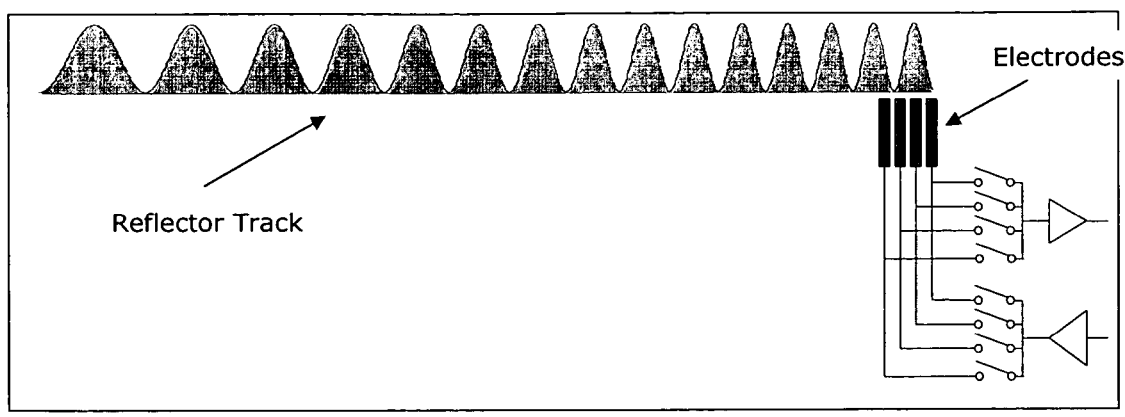
Figure 6:
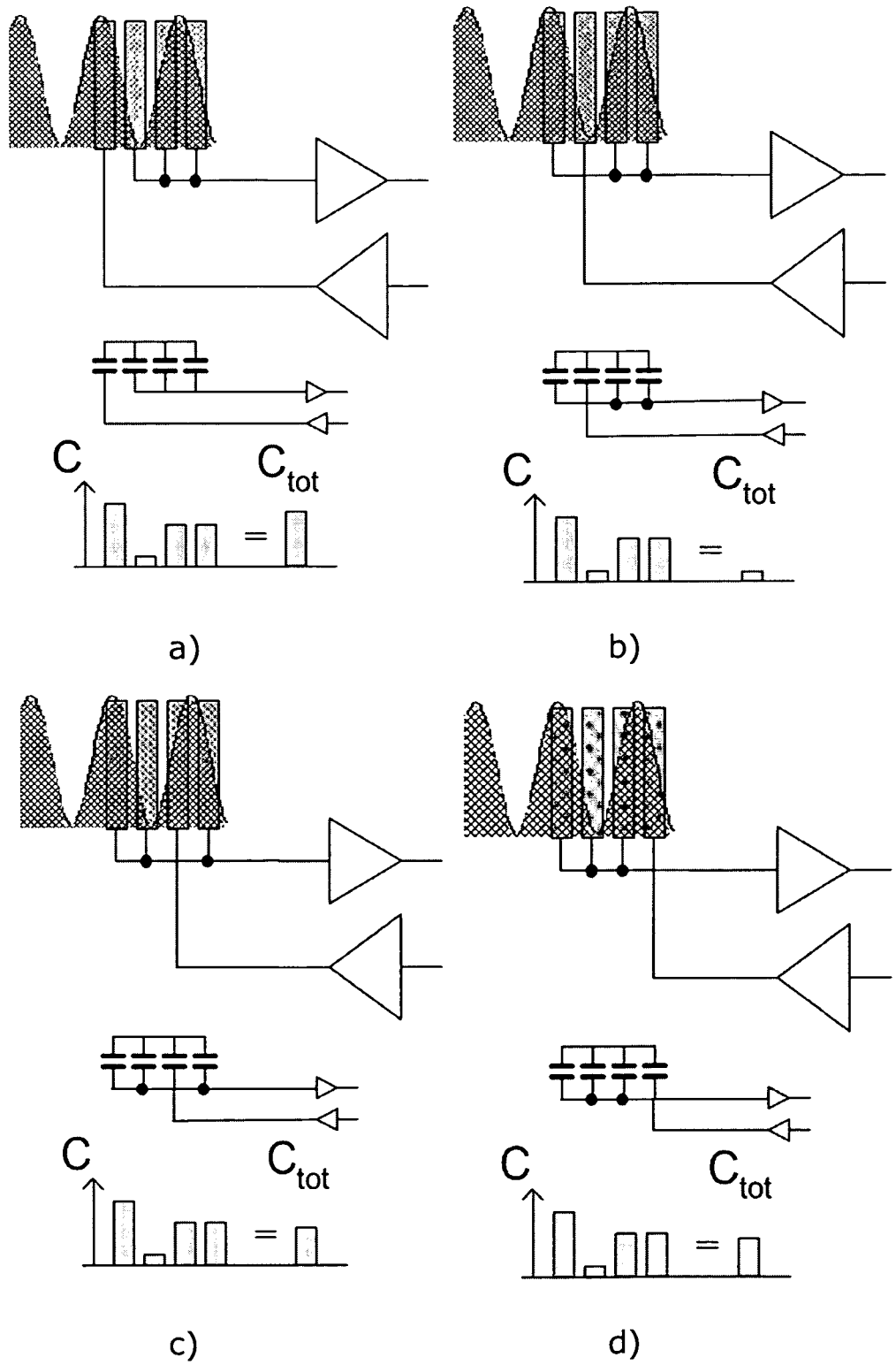
Figure 7:
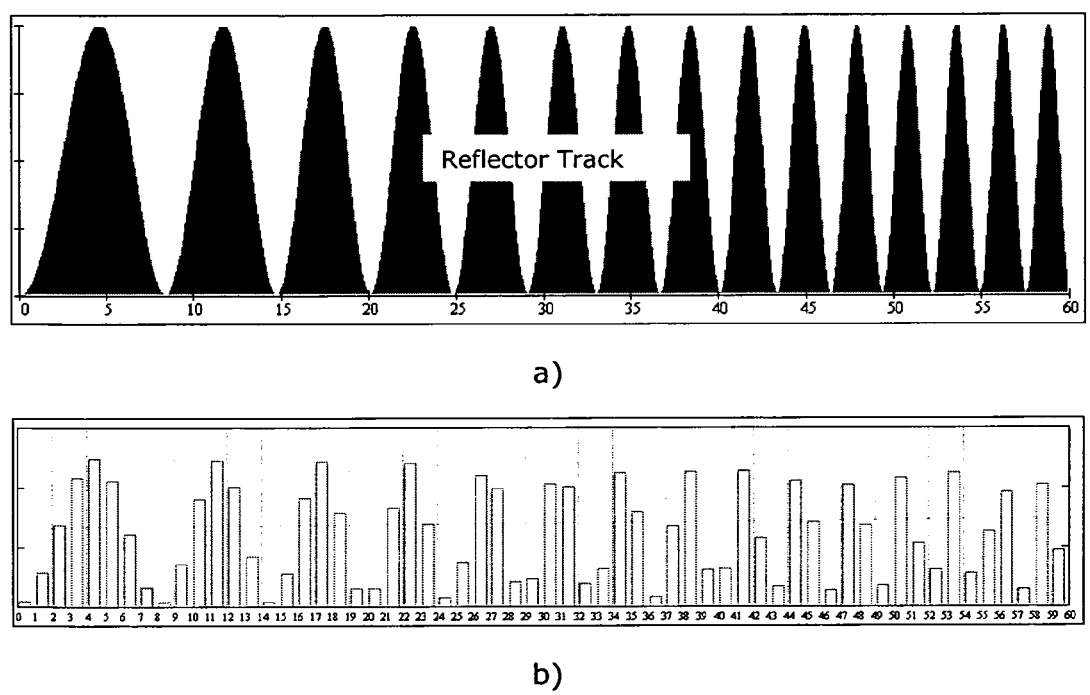

The present invention will now be described in further details with reference to the accompanying figures, wherein FIG. 1 depicts the principle behind the present invention, FIG. 2 shows two reflector tracks and a pair of emitters and one receiver associated with each track, FIG. 3 shows a section of two reflector tracks and a pair of emitters and one receiver associated with each track, FIG. 4 shows two reflector tracks with monotonically varying width, FIG. 5 shows a single reflector track with a monotonically varying reflector period, FIG. 6 shows various emitter/receiver configurations, FIG. 7 shows a single reflector track with a monotonically varying reflector period, the reflector track being divided into 60 discrete positions, each position being associated with a given capacitance, and FIG. 8 shows a medication delivery device with tracks of reflectors arranged around the dose indicator barrel.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION OF THE INVENTION

In its most general aspect, the present invention relates to a contact free position determining arrangement for determining an absolute angular position of a dose setting member of a medication delivery device. The absolute angular position of the dose setting member, which indicates the dose of medicament to be injected from the medication delivery device, is determined by applying information from a capacitive or inductive coupling between emitters and receivers both arranged on a non-rotating member of the medication delivery device, such as the housing of the medication delivery device. The coupling between emitters and receivers is established via reflectors arranged on a rotating member, such as on a dose indicator barrel of the medication delivery device. The reflectors are arranged in one or more tracks having a helical, circular or linear shape. The arrangement according to the present invention can be used for both setting a dose to be injected from the medication delivery device and for determining an amount of medicament actually injected from the medication delivery device.

The electrical coupling between emitters and receivers via the reflectors can be provided as a capacitive coupling or an inductive coupling. In case of a capacitive coupling the emitters, receivers and reflectors are implemented as essentially planar structures defining capacitor plates. In case of an inductive coupling the emitters, receivers and reflectors are implemented as inductors, such as coils, formed on for example a flex print.

Generally signals are transmitted from the emitters to the receivers (via the reflectors) by applying a digital clock signal to the emitters. For example, two emitters, which as electrically coupled to the same track of reflectors, can both be supplied with a digital clock signal around 100 kHz. However, the two clock signals provided to the two emitters are 180 degrees out of phase.

In order to avoid mixing of the signals between two neighbouring tracks of reflectors, the digital clock signals are frequency shifted meaning that the signals are frequency shifted by 8-10%. Thus, if a 100 kHz digital clock signal is provided to emitters electrically coupled to a first track of reflectors, other emitters, electrically coupled to a second track of reflectors, are provided with a 108-110 kHz clock signal.

Receivers, for example positioned between two emitters, detect the varying capacity between emitters, reflectors and receivers when the reflectors are moved relative to the emitters and receivers.

FIG. 1 illustrates the general principle behind the present invention. The arrangement depicted in FIG. 1 comprises a fixed upper part and a moveable lower part (indicated with the arrows). On the upper part a pair of emitters 1 and 3 are positioned on each side of a receiver 2. On the moveable part a single reflector element 4 is depicted. As seen, emitter 1, the reflector and the receiver 2 form a capacitor being constituted by two capacitors coupled in series. Similarly, emitter 3, the reflector and the receiver 2 also form a capacitor being constituted by two capacitors coupled in series. Evidently, the capacitances of these two capacitors are dependent on the position of the reflector relative to the emitters and the receiver. Digital clock signals around 100 kHz are provided to each of the emitters. However, the two clock signals are 180 degrees out of phase. While each of the emitters 1 and 3 is provided with a digital clock signal the receiver 2 picks up the signals transmitted by the capacitors—i.e. transmitted from each of the emitters 1 and 3 and to the receiver 2. The picked up signals are forwarded to a signal processor where the position of the upper part relative to the lower part is determined according to well-known techniques.

FIG. 2 shows two tracks of reflectors—track 1 and track 2. As seen in FIG. 2, track 1 has a shorter period than track 2. After approximately 7 periods track 2, having the longest period, is almost back to its original position. A pair of emitters and 1 receiver is associated with each track. Since track 1 has a shorter period than track 2 the emitter-receiver-emitter arrangement associated with track 1 is shorter than the corresponding emitter-receiver-emitter arrangement of track 2. During use, the emitter-receiver-emitter arrangement associated with track 1 is moved along the axial direction of track 1. Similarly, the emitter-receiver-emitter arrangement associated with track 2 is moved along the axial direction of track 2.

FIG. 3 illustrates the relative movement between two tracks of reflectors and a pair of emitters U0 and U180 and a receiver positioned between the emitters. The reflectors are positioned on a rotating part of a medication delivery device, such as on the dose setting member, whereas the emitters and the receivers are positioned on a none-rotating part of the medication delivery device, such as on the housing of the medication delivery device. The length of the reflectors of the upper track is slightly shorter than the length of the reflectors of the lower track. The lengths difference would typically be around 10%. As depicted in FIG. 3, the reflectors are repeated along both tracks. In use the emitter-receiver-emitter arrangement is moved along the axial direction of the reflector tracks and the signals picked up by the two receivers are constantly fed to a signal processor. In the depicted embodiment, the signals from the emitters U0 and U180 are capacitively coupled to the receivers.

The signals picked up by the receivers constitute a weighted sum of the signals generated by U0 and U180. Thus, if the reflector is aligned with U0 and the receiver, the picked up signal is dominated by the U0 signal. Similarly, if the reflector is aligned with U180 and the receiver, the picked up signal is dominated by the U180 signal. Thus, the picked up signal is strongly dependent on the relative position of the emitter-receiver-emitter arrangement and the reflector. If the emitter-receiver-emitter arrangement is moved over several reflector periods a periodic signal is picked up for each track. These periodic signals, one from each track, are depicted in FIG. 2. In order to avoid mixing of signals between the two tracks depicted in FIGS. 2 and 3, the frequency of the signal applied to emitters 1 and 3 is frequency shifted relative to the signal applied to emitters 1' and 3'. This frequency shift is of the order of 8-10%.

FIG. 4 shows another embodiment of the present invention. In FIG. 4 the reflector tracks R1 and R2 are formed as unbroken tracks with monotonically increasing/decreasing widths. The emitters G1 and G2 are each provided with digital clock signals of around 100 kHz. The receivers S1 and S4 pick up the signals as G1, G2, S1 and S4 move along the axial direction of R1 and R2. As with the embodiment shown in FIG. 3 the digital clock signals are capacitively coupled from the emitters G1 and G2 to the receivers S1 and S4. The position of G1, G2, S1 and S4 is determined by comparing the determined capacitance with values of a look-up table where a range of capacitance values are associated with positions along the axial direction of R1 and R2.

FIG. 5 shows a third embodiment of the present invention. In contrast to the previously shown embodiments the embodiment of FIG. 5 applies only a single track of reflectors attached to the dose setting member (not shown) of the medication delivery device. In this single track of reflectors the shape of the reflectors are varied in a sinusoidal manner along the axial direction of the track. In addition to the sinusoidal variation of the shape of the reflectors the period of the reflectors is monotonically increased/decreased. A set of four electrodes attached to the housing of the medication delivery device is applied to detect the position, and thereby the setting, of the dose setting member relative to the housing. These four electrodes are rectangular in shape and they are closely positioned. The position of the four electrodes relative to the track of reflectors, i.e. the setting of the dose setting member in relation to the housing of the medication delivery device, is obtained by applying, in an alternating manner, one of the electrodes as emitter and the other electrodes as one single receiver. This is illustrated in FIGS. 6a-d where the capacitance, for a given position along the track of reflectors, is determined for four different emitter/receiver configurations. The total capacitances for 60 discrete positions along the track of reflectors are illustrated in FIG. 7b.

Referring now to FIG. 6a the electrode to the left is driven as emitter whereas the remaining three electrodes to the right are operated as one single receiver. In this first configuration a given signal is capacitively coupled from the emitter to the receivers. This given signal is associated with a given total capacitance between emitter and receiver. Referring now to FIG. 6b the second electrode from the left is used as emitter whereas the first, third and fourth electrodes are used as one common receiver. Similarly in FIG. 6c the third electrode from the left is used as emitter whereas the first, second and fourth electrodes are used as one common receiver. Finally in FIG. 6d the last electrode is used as emitter whereas the first, second and third electrodes are used as one common receiver. Evidently, the capacitance from emitter to receivers via a reflector is dependent on the configuration of the system, i.e. which of the electrodes that are operated as emitter and receivers. The total capacitances $C_{total}$ for the different configurations are illustrated in FIGS. 6a-6d.

FIG. 7a shows a sinusoidal reflector pattern comprising a total of 15 periods. The ratio between the width of the first period and the width of the last period is 4. Dividing these 15 periods into 60 units (60 IU) the capacitance associated with each of these 60 discrete positions can be determined—see FIG. 7b. This dividing onto 60 discrete positions sets the angular resolution of the dose setting member of the medication delivery device. Thus, the dose setting member of the medication delivery device is positionable in 60 discrete positions from start to end. The 60 discrete positions may be disposed over more than one revolution of the dose setting member, such as 2 or 3 revolutions or even more. However, the number of revolutions need not be an integral number. It should be noted that a few of the capacitance values depicted in FIG. 7b could appear to be of similar values. However, this is obviously not the case—thus, all depicted capacitances are of different values.

FIG. 8 shows a pair of reflector tracks arranged on a dose indicator barrel. As depicted, the two tracks are arranged in a parallel manner and each track forms an essentially helical track around the dose indicator barrel.

The invention claimed is:

1. A contact free arrangement in a medication delivery device for determining an absolute position of a first member moveably mounted relative to a second member, the first member being rotatably mounted and restricted for movement between a first end position and a second end position over an angle of rotation exceeding one revolution, the contact free arrangement comprising:
   at least one track of reflector means arranged on the first member,
   at least one emitter means arranged on the second member, the at least one emitter means being adapted to electrically couple to a number of the reflector means, and
   at least one receiver means arranged on the second member, the at least one receiver means being adapted to electrically couple to a number of the reflector means,
   generator means for generating a signal or signals and providing such signal(s) to the at least one emitter means, and processor means for processing a signal or signals from the at least one receiver means;
   wherein the at least one track of reflector means forms a helical path and, wherein the at least one track of reflector means, the at least one emitter means, the at least one receiver means and the generator means are arranged in such a manner that there is provided a different electrical parameter to each respective position of the first member relative to the second member, said electrical parameter being selected from the group consisting of capacitance and inductance.

2. The contact free arrangement according to claim 1, further comprising a different electrical parameter for each respective position of the first member relative to the second member for movement of the first member in the range between the first end position and the second end position.

3. The contact free arrangement according to claim 1 comprising a single track of reflector means.

4. The contact free arrangement according to claim 3, wherein the single track of reflector means comprises a helical-shaped row of electrically conducting members arranged on the first member of the medication delivery device, and the electrically conducting members forming the track varies monotonically along an axial direction of the row.

5. The contact free arrangement according to claim 1, comprising a first and a second track of reflector means, the first and second tracks of reflector means being arranged in a substantially parallel manner.

6. The contact free arrangement according to claim 5, wherein the first track of reflector means comprises a helical-shaped row of electrically conducting members arranged on the first member of the medication delivery device, the electrically conducting members of the first track defining a first period, and wherein the second track of reflector means comprises a helical-shaped row of electrically conducting members arranged on the first member of the medication delivery device, the electrically conducting members of the second track defining a second period, the first period being different from the second period.

7. The contact free arrangement according to claim 1, wherein the second member is a non-rotatably mounted part of the medication delivery device.

8. The contact free arrangement according to claim 5, wherein the first and second tracks of reflector means each comprises an essentially unbroken path of an electrically conducting material, each of said first and second essentially unbroken paths of electrically conducting material having a width which varies along an axial direction of the track.

9. The contact free arrangement according to claim 1, wherein the at least one emitter and a number of the reflector means form a capacitor in combination.

10. The contact free arrangement according to claim 1, wherein the at least one receiver and a number of the reflector means form a capacitor in combination.

11. The contact free arrangement according to claim 1, wherein the at least one emitter and a number of the reflector means are adapted to couple in an inductive manner.

12. The contact free arrangement according to claim 1, wherein the at least one receiver and a number of the reflector means are adapted to couple in an inductive manner.

13. The contact free arrangement according to claim 11 wherein the at least one emitter and the at east one receiver comprise a coil adapted for generating and receiving a magnetic field, respectively.

14. The contact free arrangement according to claim 11, wherein a number of the reflector means are configured so as to support eddy currents induced by the emitters.

15. The contact free arrangement according to claim 1, comprising, for each track of reflector means, two emitter means and one receiver means.

16. The contact free arrangement according to claim 15, wherein, for each track of reflector means, the two emitter means and the one receiver means are arranged along a substantially straight line, and wherein the one receiver means is arranged between the two emitter means.

17. A medication delivery device or a syringe comprising the arrangement according to claim 1.

18. A method for contact free determination of an absolute position of a first member moveably mounted relative to a second member in a medication delivery device, the first member being rotatably mounted and restricted for movement between a first end position and a second end position over an angle of rotation exceeding one revolution, the method comprising:
providing at least one track of reflector means arranged on the first member,
providing an electrical signal to at least one emitter means arranged on the second member, the at least one emitter means being electrically coupled to a number of the reflector means, and
receiving an electrical signal from at least one receiver means arranged on the second member, the at least one receiver means being electrically coupled to a number of the reflector means,
providing a generator means for generating a signal or signals and providing such signal(s) to the at least one emitter means, and processor means for processing a signal or signals from the at least one receiver means,
providing an electrical signal to at least one emitter means by means of said generator means, and
receiving an electrical signal from at least one receiver means and processing said received signal by means of the processor means to determine the absolute angular position of the first member relative to the second member,
wherein the at least one track of reflector means forms a helical path and, wherein the at least one track of reflector means, the at least one emitter means, the at least one receiver means and the generator means are arranged in such a manner that there is provided different electrical parameter to each respective position of the first member relative to the second member, said electrical parameter being selected from a group consisting of capacitance and inductance.

19. The method according to claim 18, wherein a first electrical signal is provided to a first emitter, and wherein a second electrical signal is provided to a second emitter, the first and second electrical signals being approximately 180 degrees out of phase.

20. The method according to claim 19, wherein the electrical signals provided to the first and second emitters oscillate with a frequency within the range 50 kHz-150 kHz.

21. The method according to claim 19, wherein the frequency of the first electrical signal is different than the frequency of the second electrical signal.

22. The method according to claim 21, wherein the frequency of the second electrical signal is shifted 8-10% relative to the frequency of the first electrical signal.

23. The method according to claim 20, wherein the electrical signals provided to the first and second emitters oscillate with a frequency within the range of 90 kHz-110 kHz.

24. The method according to claim 18, further comprising a different electrical parameter for each respective position of the first member relative to the second member for movement of the first member in the range between the first end position and the second end position.

* * * * *

UNITED STATES PATENT AND TRADEMARK OFFICE
CERTIFICATE OF CORRECTION

| | |
|---|---|
| PATENT NO. | : 8,638,108 B2 |
| APPLICATION NO. | : 12/067472 |
| DATED | : January 28, 2014 |
| INVENTOR(S) | : Neilsen et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1435 days.

Signed and Sealed this
Seventh Day of July, 2015

Michelle K. Lee
*Director of the United States Patent and Trademark Office*